United States Patent [19]
Rossi et al.

[11] Patent Number: 6,096,715
[45] Date of Patent: *Aug. 1, 2000

[54] CHIMERIC DNA-RNA CATALYTIC SEQUENCES

[75] Inventors: John J. Rossi, Glendora; Nerida Taylor, Loma Linda, both of Calif.

[73] Assignee: City of Hope, Duarte, Calif.

[ * ] Notice: This patent is subject to a terminal disclaimer.

[21] Appl. No.: 08/058,660

[22] Filed: May 7, 1993

[51] Int. Cl.⁷ ...................................... C07H 21/04
[52] U.S. Cl. .............................. 514/44; 536/24.5
[58] Field of Search ................. 435/6; 536/23.1, 536/24.5; 514/44

[56] References Cited

PUBLICATIONS

Taylor et al, Nucleic Acids Res., v. 201, N. 17, 1992, pp. 4559–4565.

*Primary Examiner*—James Ketter
*Attorney, Agent, or Firm*—Rothwell, Figg, Ernst & Kurz

[57] ABSTRACT

A chimeric RNA-DNA ribozyme, the catalytic center of which is linked to a stem and loop structure. The stem and loop structure may be RNA, DNA, or mixed RNA and DNA sequences.

4 Claims, No Drawings

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 47
      (B) TYPE: Nucleotide
      (C) STRANDEDNESS: Single
      (D) TOPOLOGY: Unknown (xi) SEQUENCE DESCRIPTION: SEQ ID NO: 1:

CCGCTTAATA CUCUGAUGAG TCCGTGAGGA CGAAACGCTC TCGCACC      47

(2) INFORMATION FOR SEQ ID NO: 2:

(i) SEQUENCE CHARACTERISTICS:
      (A) LENGTH: 47
      (B) TYPE: Nucleotide
      (C) STRANDEDNESS: Single
      (D) TOPOLOGY: Unknown (xi) SEQUENCE DESCRIPTION: SEQ ID NO: 2:

CCGCTTAATA CUCUGAUGAG UCCGUGAGGA CGAAACGCTC TCGCACC      47

(2) INFORMATION FOR SEQ ID NO: 3:

(i) SEQUENCE CHARACTERISTICS:
      (A) LENGTH: 32
      (B) TYPE: Nucleotide
      (C) STRANDEDNESS: Single
      (D) TOPOLOGY: Unknown (xi) SEQUENCE DESCRIPTION: SEQ ID NO: 3:

CGAUGGUGCG AGAGCGUCAG UAUUAAGCGG AU      32

(2) INFORMATION FOR SEQ ID NO: 4:

(i) SEQUENCE CHARACTERISTICS:
      (A) LENGTH: 26
      (B) TYPE: Nucleotide
      (C) STRANDEDNESS: Single
      (D) TOPOLOGY: Unknown (xi) SEQUENCE DESCRIPTION: SEQ ID NO: 4:

GGTGCGAGAG CGUCAGTATT AAGCGG      26

CHIMERIC DNA-RNA CATALYTIC SEQUENCES

This invention was made with government support under Grant Nos. AI25959 and AI39239 awarded by the National Institutes of Health. The government has certain rights in the invention.

FIELD OF THE INVENTION

This invention pertains to chimeric DNA-RNA-DNA catalytic molecules or ribozymes.

BACKGROUND OF THE INVENTION

Ribozymes are RNA molecules capable of cleaving specific RNA sequences(1), (2), (3).1/ Perreault (4) describes ribozymes in which the ribose sugars of core nucleotides are replaced with deoxyribose sugars. Chimeric ribozymes are exemplified in U.S. Pat. Nos. 5,144,019 and 5,149,796.

1/ A Bibliography precedes the claims.

SUMMARY OF THE INVENTION

This invention provides chimeric hammerhead ribozymes of a kind described in Taylor (5). These ribozymes consist essentially of first and second deoxyribonucleotide sequence stems I and III which are complementary to the sequences adjacent the cleavage site of an RNA substrate. Stem I and stem III flank a catalytic center joined to a nucleotide sequence forming stem II which terminates in a loop II.

The chimeric ribozymes of the invention have the schematic formula I:

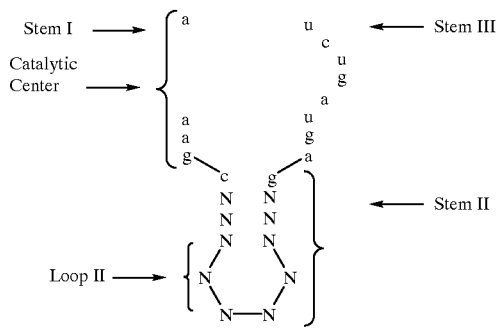

in which N may be any nucleotide.

Stems I and III are deoxyribonucleotide sequences each preferably 6 to 20 bases in length. The bases forming the catalytic center are all ribonucleotides. Stem II and loop II may be all ribonucleotides, all deoxyribonucleotides or any desired combination of ribo- and deoxyribonucleotides. In preferred embodiments, stem II and loop II include only ribodeoxynucleotides.

In one preferred form of the invention, stem II and loop II have the schematic formula:

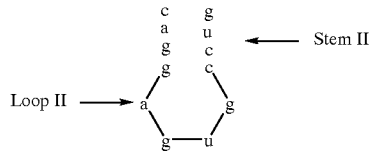

DETAILED DESCRIPTION OF THE INVENTION

Synthesis of Ribozymes and Substrates

Three anti-HIV-1 gag ribozymes of identical base sequence but differing in RNA-DNA content were synthesized. rzGH is an all RNA ribozyme, whereas rzDRD and rzLoop have DNA in stems I and III. rzDRD also has DNA in stem loop II.

The formulae for rzDRD is shown by SEQ ID NO: 1: 5' CCGCTTAATACucugaugaGTCCGTGAG-GACgaaaCGCTCTCGCACC 3'.

The formulae for rzLoop is shown by SEQ ID NO: 2: 5' CCGCTTAATACucugaugaguccgugag-gacgaaaCGCTCTCGCACC 3'.

In SEQ ID NO's: 1 and 2, lower case letters represent ribonucleotides and capital letters represent deoxyribonucleotides.

Assembly of mixed oligodeoxyribo- and ribonucleotides was performed on an automated synthesizer (Applied Biosystems 380B). 5'-dimethoxytrityl, 2'-tertbutylsilyl, and N-acyl (benzoyl for adenosine and cytosine, isobutyrl for guanosine) ribonucleoside cyanoethyl phosphoramidites (American Bionetics) were used for synthesis of the RNA segments. 5'-dimethoxytrityl, N-protected deoxynucleoside phosphoramidites (American Bionetics) and the derivatized LCAA-CPG were used for synthesis of the DNA. HPLC-grade acetonitrile was refluxed and distilled over $CaH_2$. THF for the capping solution was dried over activated 4-A molecular sieves prior to use. Tetrazole (Aldrich Chemical Co.) was recrystallized from dry acetonitrile and then dried under vacuum and stored under argon.

The synthesizer was programmed such that the RNA was coupled using an RNA-synthetic cycle (720 seconds coupling time) and the DNA units were assembled by a DNA-synthetic cycle. The standard synthetic cycle (Applied Biosystems) was modified by the introduction of neutralization with 3% TEA in acetonitrile after detritylation. The average coupling yield, determined by UV quantitation of the released trityl cation (504 nm for DMT cation) was 97.5%.

Aqueous solutions used during deprotection and all HPLC buffers were sterilized by treatment with diethylpyrocarbonate (DEPC) (Aldrich Chemical Co.) followed by autoclaving for 1 h. All aqueous solutions and buffers contained 0.0001% $NaN_3$ to prevent bacterial growth. Only disposable, sterile plasticwares were used during the final purification. Sephadex G-25F (Pharmacia) was also sterilized. Strictly sterile conditions were maintained during purification after final deprotection.

The assembled molecules were deprotected as follows. The cyanoethyl phosphate deprotection and deacylation were provided by treatment with saturated, anhydrous ethanolic ammonia for 8 h at 55° C.(6). Deprotection with anhydrous ethanolic ammonia was found to be more reproducible and reliable than treatment with 35% aq. ammonia-ethanol(7). The products of deacylation were then treated with tetrabutylammonium fluoride (Aldrich Chemical Co.), at a 1 M concentration in THF for 30 h at room temperature to remove the 2'-OH silyl protecting groups from the RNA. The final product was then desalted on a Sephadex G-25 column, and purified by HPLC on a 4×250 mm PRP (Hamilton) column using a 0% (A) - 100% (B) linear gradient (25 minute running time) of (A) 0.005 M triethyl ammonium acetate-water, pH 6.,5 and (B) 0.005 M triethylammonium acetate-water, pH 6.,5 in acetonitrile, 2:3.

An alternative method for purification of the totally deprotected oligodeoxyribo- and ribonucleotides after final treatment with tetrabutylammonium fluoride involves dialysis of the reaction mixture against water (using a 3000-molecular-weight cutoff membrane) followed by HPLC on a Vydac oligonucleotide ion-exchange column. Although this procedure is time-consuming, it is a more reliable method for purification of deprotected synthetic RNA.

For the final purification, the chimeric oligonucleotides were washed twice in DEPC-treated water, concentrated by drying, and precipitated with ethanol. The samples were resuspended in DEPC-treated water and purified by electrophoresis in a 15% polyacrylamide, 7 M urea gel. The oligonucleotides were visualized by UV shadowing, excised, and eluted from the gel slice via diffusion in a solution of 0.3 M NaOAc, 0.1% SDS and 1 mM EDTA at 37° C. Crushed gel fragments were filtered in a Costar spin-X filter and the supernatant was precipitated with ethanol, lyophilized and resuspended in sterile DEPC-treated water. Concentrations were determined from the absorption of 260 nm. The DNA-RNA junctions of the oligomers were confirmed by RNAase A and T1 digestion of $^{32}$p end-labeled samples.

Two substrates rGAG and dGAGrUCA were subjected to cleavage by the ribozymes of SEQ ID NO: 1 and 2

(SEQ ID NO: 3)
rGAG
5'-cgauggugcgagagcgucaguauuaagcggau-3'

(SEQ ID NO: 4)
rGAGrUCA
5'-GGTGCGAGAGCGucaGTATTAAGCGG-3'

Standard cleavage reactions involved heating to 85° C. for 1 min. two separate tubes containing a solution of 50mM Tris-HCl (pH 8.5) and either ribozyme (10 nM) or substrate (20–100 nM). This was followed by cooling to room temperature, addition of 20 mM MgCl$_2$ to each tube and incubation at 55° C. for 15 min. The cleavage reactions were initiated by mixing equal volumes of the target and ribozyme mixtures for a typical final volume of 10 µl per reaction time point. In order to denature the ribozyme-product complexes, a 25% volume of 90% formamide loading solution was added and the samples were heated to 85° C. for one minute, chilled on ice and electrophoresed in a 15% polyacrylamide, 7 M urea gel. Quantitations of cleavage were performed on an Ambis radioanalytic imaging system.

Temperature profile reactions did not include preincubation. A 12 µl volume containing 10 nM ribozyme and 40 nM target in 50 mM Tris-HCl (pH 8.5) was mixed with 3 µl of 100 mM MgCl$_2$ to start the reaction. All reactions were stopped by the addition of 3 µl of 200 mM EDTA. Some non-specific breakdown of substrate was observed at temperatures above 60° C.

For kinetic determinations, the reactions were performed as described above for standard cleavage. Substrate concentrations in 4 to 12-fold excess of the ribozyme concentration (0.05 or 0.1 pmol/10 µl reaction volume) were used and time points were selected to represent the linear burst and steady-state velocity phases of the catalyst-substrate pair being tested. Calculations of $K_m$, $K_{mb}$, $\kappa_{cat}$ and $\kappa_{catb}$ were derived from both Eadie-Hofstee (8) and direct linear plots (9).

For the sake of simplicity, use was made of the kinetic equation:

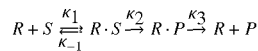

where R equals ribozyme, S equals substrate and P equals the products of cleavage. Hence, the constants $\kappa_2$ and $\kappa_3$ refer to cleavage and dissociation of R from P, respectively. Using Briggs-Haldane analyses of the data, the turnover number, $K_{cat}$ can be determined ($\kappa_{cat}=V_{max}$/E, where E is the enzyme concentration).

The velocity profiles of some ribozymes are biphasic. Such profiles show a dramatic increase in velocity after one enzyme equivalent of substrate has been cleaved. See, e.g., FIG. 3 of Taylor(5). This phenomenon has been described previously for protein enzymes and has been labeled burst kinetics (10). The initial burst velocity, b, can be distinguished from the steady state velocity, v, that follows it. Bender, et al. (11) derived the following equation for the burst velocity (where $S_o$ is the initial substrate concentration):

$$b=[(\kappa_2+\kappa_3)S_o+\kappa_3 Ks]/(K_s+S_o)$$

This equation can be reduced to $$b=[(\kappa_2+\kappa_3)S_o]/(K_s+S_o)$$

when b>>$\kappa_3$ (12). This allows for Michaelis-Menten type kinetic analysis of b with changing initial substrate concentration, $S_o$, and leads to the determination of $K_s$ and ($\kappa_2+\kappa_3$) rather than $K_m$ and $V_{max}$.

Burst kinetics are seen only when the rate-limiting step of the reaction occurs after the measured chemical step. In the case of ribozyme-mediated cleavage, burst kinetics imply that the rate of the measured step, cleavage, is fast compared to the rate-limiting step which is product dissociation.

RESULTS

The effects of incorporating DNA within the nonconserved portion of a hammerhead ribozyme were examined by synthesizing the 47-nucleotide DNA-RNA chimeric catalyst rz.DRD, which contained only 12 ribonucleotides, all in the highly conserved catalytic center. Stem-loop II was comprised entirely of deoxyribonucleotides. The kinetic parameters of this chimeric ribozyme were determined alongside those of an all-RNA ribozyme (rz.GH) of identical length and sequence.

Cleavage reactions were performed over a wide range of temperatures in order to assess the temperature at which the rz.DRD ribozyme optimally cleaved an RNA substrate. See FIG. 2 of Taylor(5). The temperature optimum for RNA cleavage by rz.DRD was ca. 55° C., as compared to an optimum of ca. 65° C. for rz.GH, suggesting that DNA-RNA hybrid helix is less stable than the RNA-RNA helix for this sequence.

The plot of time versus cleavage product formation for the ribozyme rz.GH and the RNA substrate rGAG showed biphasic velocity. See FIG. 3 of Taylor(5). This type of profile, a burst velocity followed by a slower steady-state velocity, is well documented for protein enzymes (9, 11, 12). In the present case, when a sixfold substrate excess was used, the "burst" velocity for the first turnover was 3.5 times faster than the subsequent steady-state velocity. See FIG. 3 of Taylor(5). In contrast, the chimeric ribozyme rz.DRD of Formula IV did not show a comparable burst velocity. See FIG. 3 of Taylor(5). The kinetic data (Table 1) demonstrate a steady state $\kappa_{cat}$ for rz.DRD equivalent to that of rz.GH (0.019/min), while the $K_m$ of rz.DRD for the RNA substrate was almost twice that of rz.GH.

TABLE 1

Kinetic Parameters of Chimeric Ribozymes and Substrates

| Ribozyme | Substrate | $K_{mb}$ (nM) | $K_{catb}$ (/min) | $K_m$ (nM) | $K_{cat}$ (/min) |
|---|---|---|---|---|---|
| rz.GH | rGAG | 31 | 0.25 | 38 | 0.019 |
| rz.GH | dGAGrUCA | | | 56 | 0.087 |
| rz.DRD | rGAG | | | 64 | 0.019 |
| rz.DRD | dGAGrUCA | | | 196 | 0.024 |
| rz.DRD | dGAGrUCA (50° C.) | | | 48 | 0.012 |
| rz.RLoop | rGAG | 51 | 0.27 | 64 | 0.126 |
| rz.RLoop | dGAGrUCA | | | 91 | 0.108 |

* All measurements were taken at 55° C. unless specified.

The absence of burst velocity for rz.DRD suggested that product dissociation was not rate-limiting for this ribozyme, and hence another step in the ribozyme catalysis pathway was rate limiting. To determine whether or not the hybrid helices were responsible for this altered activity, a chimeric DNA-RNA substrate, dGAGrUCA, was synthesized. In this substrate, all of the base pairing sequences are DNA, except for the nucleotide at the site of cleavage and the two nucleotides flanking the cleavage site. The annealing of this substrate with rz.GH reverses the positions of DNA and RNA with stems I and III, as compared to rz.DRD and the rGAG substrate.

As was observed for all RNA chimeric ribozyme, rz.DRD, the chimeric substrate-rz.GH combination had a temperature optimum of ca. 55° C. Cleavage of dGAGrUCA by rz.GH did not result in a burst velocity. The steady-state velocity was intermediate to that of the rz.GH-rGAG burst and steady-state velocities. The $\kappa_{cat}$ determined for rz.GH cleavage of dGAGrUCA was 4.5-fold faster than cleavage of rGAG with either rz.GH or rz.DRD (Table 1). The $K_m$ for rz.GH with the dGAGrUCA substrate was about twice that obtained with the RNA substrate rGAG. The chimeric substrate dGAGrUCA could also be cleaved by the chimeric ribozyme rz.DRD, yielding the following kinetic values: at 50° C. (the optimal temperature for cleavage using the chimeric ribozyme-chimeric substrate combination) the $K_m$ was 48 nM an the $\kappa_{cat}$ 0.012/min.

Since rz.DRD had reduced cleavage activity relative to rz.GH, another chimeric ribozyme (rz.RLoop) was synthesized in which only the base-pairing sequences were DNA, and the catalytic center as well as stem-loop II were RNA (Formula I). Like the other DNA-RNA hybrid helix-forming combinations (rz.DRD-rGAG and rz.GH-dGAGrUCA), the temperature optimum for cleavage by rz.RLoop was ca. 55° C. When rz.RLoop was analyzed with the rGAG substrate, a burst velocity was in fact observed. See FIG. 3 of Taylor (5). A second rate change in product formation was observed for both rz.RLoop and rz.GH with rGAG when approximately one-fourth of the substrate had been cleaved, and most probably reflects product inhibition (ibid).

The burst phase kinetic constants determined for the chimeric ribozyme rz.RLoop (Formula I) are comparable to those for the all-RNA ribozyme rz.GH (Table 1). In contrast, the steady state $\kappa_{cat}$ for rz.RLoop is six times faster than that determined for rz.GH (0.126/min versus 0.02/min). The $K_m$ and $K_{mb}$ for rz.RLoop with rGAG were slightly greater than those obtained for rz.GH with rGAG. The kinetic constants determined for rz.RLoop with the chimeric dGAGrUCA substrate demonstrated a slightly higher $K_m$ value and a somewhat slower $\kappa_{cat}$ value than were obtained with the rGAG substrate (Table 1).

The relative stabilities of the chimeric ribozymes versus RNA ribozymes were assessed in cell culture experiments. RNA and chimeric ribozymes were first incubated with H9 lymphocytes in serum containing culture media. The RNA molecules were completely degraded within one hour of incubation, whereas the chimeric ribozymes were relatively stable for several hours, and found associated with H9 lymphocytes, either adhered to the cell membrane, or intracellularly (data not presented). Since stabilization of the RNA in cell culture was not achieved, a commercial cationic liposome preparation was utilized to deliver both the RNA and chimeric molecules to the H9 lymphocytes to evaluate the relative intracellular stabilities of the two ribozyme preparations. Total RNA (including the chimeric ribozymes) was extracted at varying times following the transfection. The data presented in Table 2 suggests that it is the DNA in the flanking sequences which provides substantial intracellular stabilization of rz.RLoop (Formula I) when compared to the all-RNA ribozyme for rz.GH (Formula II), resulting in approximately threefold greater recovery after 48 hours of incubation.

TABLE 2

The in vivo stability of chimeric (rz.RLoop) (Formula I) and RNA (rz.GH) (Formula II) ribozymes in H9 lymphocytes following Lipofectin transfection

| Time following transfection (h) | rz.GH 32p-labeled (% remaining*) | rz.RLoop 35s-labeled (% remaining*) | rz.RLoop 32p-labeled (% remaining*) |
|---|---|---|---|
| 2 | 100.0 | 100.0 | +++ |
| 6 | 87.3 | 87.4 | 100.0 |
| 12 | 53.4 | 80.3 | 78.2% |
| 24 | 47.9 | 83.7 | +++ |
| 36 | 31.3 | +++ | 74.7% |
| 48 | 21.6 | 70.6 | 60.4% |

*The percentage of the counts at first time point that remain.
+++ Data not available.

BIBLIOGRAPHY

1. Cotten, M., *Tibtech.* 8:174–178 (1990).

2. Rossi, J.J., et al., *Tibtech* 8:179–183 (1990).

3. Cech, T., *JAMA* 260:3030–3034 (1988).

4. Perreault, et al., *Nature,* 344:565–567 (1990).

5. Taylor, et al., *Nucleic Acids Res.* 20:4559–4565 (1992).

6. Scaringe, et al., *Nucleic Acids Res.* 18:5433–5441 (1990).

7. Stawinski, et al., *Nucleic Acids Res.* 16:9285–9298 (1988).

8. Hofstee, *J.Am.Chem.Soc.* 184:1296–1298 (1959).

9. Eistenthal, et al., *Biochem.J.* 139:715–720 (1974).

10. Kezdy, et al., *Biochemistry* 1:1097–1106 (1962).

11. Bender, et al., *J.Chem.Educ.* 44:84–88 (1967).

12. Taylor, Unpublished PhD thesis, Loma Linda University, Loma Linda, Calif. (1992).

---

We claim:

1. A chimeric ribozyme having first and second oligodeoxyribonucleotide sequences which are complementary to the sequences adjacent to the cleavage site of an RNA substrate, wherein said first and second sequences flank an oligoribonucleotide sequence forming the catalytic center and a stem and loop structure, said oligoribonucleotide sequence having the formula:

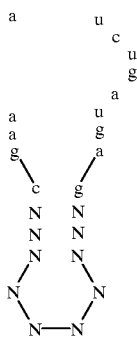
wherein N represents any ribonucleotide.
2. The chimeric ribozyme of claim 1, having the formula:
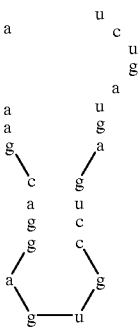
3. SEQ ID NO. 1.
4. SEQ ID NO. 2.
* * * * *